US011065301B2

(12) United States Patent
Kalergis Parra et al.

(10) Patent No.: US 11,065,301 B2
(45) Date of Patent: Jul. 20, 2021

(54) PHARMACEUTICAL COMPOSITION FOR AMELIORATING THE SYMPTOMS AND DISEASE OF THE RESPIRATORY INFECTION CAUSED BY HUMAN METAPNEUMOVIRUS (HMPV), WHICH COMPRISES AT LEAST ONE AGENT THAT NEUTRALIZES THE FUNCTION OF TSLP AND/OR TSLPR AND/OR OX40L AND/OR CD177 MOLECULES, AND A PHARMACEUTICALLY ACCEPTABLE EXCIPIENT, AND USE THEREOF (71) Applicant: PONTIFICIA UNIVERSIDAD CATOLICA DE CHILE, Santiago (CL)

(72) Inventors: Alexis Mikes Kalergis Parra, Santiago (CL); Margarita Kam-Lem Lay Remolcoi, Santiago (CL); Susan Marcela Bueno Ramirez, Santiago (CL)

(73) Assignee: PONTIFICIA UNIVERSIDAD CATOLICA DE CHILE, Santiago (CL)

( * ) Notice: Subject to any disclaimer, the term of this patent is extended or adjusted under 35 U.S.C. 154(b) by 0 days.

(21) Appl. No.: 16/093,826

(22) PCT Filed: Apr. 15, 2016

(86) PCT No.: PCT/IB2016/052180
§ 371 (c)(1),
(2) Date: Jan. 15, 2019

(87) PCT Pub. No.: WO2017/178869
PCT Pub. Date: Oct. 19, 2017

(65) Prior Publication Data
US 2019/0125832 A1    May 2, 2019

(51) Int. Cl.
*A61K 39/395* (2006.01)
*A61K 38/17* (2006.01)
*C07K 16/00* (2006.01)
*C07K 16/28* (2006.01)
*A61P 31/14* (2006.01)

(52) U.S. Cl.
CPC ........ *A61K 38/1774* (2013.01); *A61K 39/395* (2013.01); *A61P 31/14* (2018.01); *C07K 16/00* (2013.01); *C07K 16/28* (2013.01)

(58) Field of Classification Search
CPC ............ A61K 2039/505; A61K 39/001; A61K 39/001118; A61K 47/6843; A61K 2039/53; A61K 39/12; A61K 38/1774; A61K 39/395; A61K 38/00; A61K 45/06; A61K 38/1793; A61K 2039/572; C07K 2317/515; C07K 16/00; C07K 16/28; C12Q 1/6823; B01L 3/502761; A61P 31/14; A61P 31/12; A61P 11/00; A61P 31/00; A61P 37/04; A61P 31/20
See application file for complete search history.

(56) References Cited

U.S. PATENT DOCUMENTS

| | | | | |
|---|---|---|---|---|
| 8,084,216 | B2 * | 12/2011 | Greinacher | .......... C12Q 1/6883 435/7.1 |
| 9,682,143 | B2 * | 6/2017 | Chang | .................... A61K 38/21 |
| 2009/0053230 | A1 | 2/2009 | Martin | |
| 2014/0099254 | A1 | 4/2014 | Chang et al. | |

FOREIGN PATENT DOCUMENTS

| | | |
|---|---|---|
| EP | 2341076 A2 | 7/2011 |
| WO | 2014082993 A2 | 6/2014 |

OTHER PUBLICATIONS

Sachs et al. JBC, 2007, vol. 282, No. 32, pp. 23603-23612.*
M.K. Lay, et al; Human metapneumovirus infection activates the TSLP pathway that drives excessive pulmonary inflammation and viral . . . ; European Journal of Immunology; vol. 45; No. 6; 2015; pp. 1680-1695.
C.E. Palavecino, et al; Understanding lung immunopathology caused by the human metapneumovirus: implications for rational vaccine design; Critical Reviews in Immunology; vol. 35; No. 3; 2015; pp. 185-202.
M. Lay, et al; Human metapneumovirus infection induces expression of thymic stromal lymphopoetin and IL-33 in airway . . . ; The Journal of Immunology; vol. 190; No. 1; 2013; Supplement; p. 189.15.
V. Soumelis, et al; Human thymic stromal lymphopoietin: a novel epithelial cell-derived cytokine and a potential key player . . . ; Springer Seminars in Immunopathology; Springer-Verlag, 2004; pp. 325-333.
S.F. Ziegler; Thymic stromal lymphopoietin and allergic disease; Journal of Allergy and Clinical Immunology; vol. 130; No. 4; 2012; pp. 845-852.

(Continued)

*Primary Examiner* — Bao Q Li
(74) *Attorney, Agent, or Firm* — Lucas & Mercanti LLP (57) ABSTRACT

The present invention relates to a pharmaceutical composition for ameliorating the symptoms and disease of the respiratory infection caused by human Metapneumovirus (hMPV), which comprises at least one agent that neutralizes the function of TSLP and/or TSLPR and/or OX40L and/or CD177 molecules, and a pharmaceutically acceptable excipient, wherein the agent is selected from monoclonal antibodies, biological or synthetic molecules. More specifically, the neutralizing agents are humanized anti-TSLP, anti-TSLPR, anti-OX40L and anti-CD177 monoclonal antibodies. The use of said composition for preparing a medicament for treating or ameliorating the symptoms and disease of patients infected with human Metapneumovirus (hMPV) is also described.

6 Claims, 7 Drawing Sheets
Specification includes a Sequence Listing.

(56) References Cited

OTHER PUBLICATIONS

J. Han, et al; Responsiveness to respiratory syncytial virus in neonates is mediated through thymic stromal lymphopoietin and OX40 ligand; J Allergy Clin Immunol; vol. 130, No. 5; Nov. 2012; 16 pages.
International Search Report dated Jan. 5, 2017 for PCT/IB2016/052180 and English translation.

* cited by examiner

```
                              SEQUENCE LISTING

<160> NUMBER OF SEQ ID NOS: 14

<210> SEQ ID NO 1
<211> LENGTH: 10
<212> TYPE: PRT
<213> ORGANISM: Rattus norvegicus

<400> SEQUENCE: 1

Gly Tyr Ile Phe Thr Asp Tyr Ala Met His
1               5                   10

<210> SEQ ID NO 2
<211> LENGTH: 17
<212> TYPE: PRT
<213> ORGANISM: Rattus norvegicus

<400> SEQUENCE: 2

Thr Phe Ile Pro Leu Leu Asp Thr Ser Asp Tyr Asn Gln Asn Phe Lys
1               5                   10                  15

Gly

<210> SEQ ID NO 3
<211> LENGTH: 11
<212> TYPE: PRT
<213> ORGANISM: Rattus norvegicus

<400> SEQUENCE: 3

Met Gly Val Thr His Ser Tyr Val Met Asp Ala
1               5                   10

<210> SEQ ID NO 4
<211> LENGTH: 11
<212> TYPE: PRT
<213> ORGANISM: Rattus norvegicus

<400> SEQUENCE: 4

Arg Ala Ser Gln Pro Ile Ser Ile Ser Val His
1               5                   10

<210> SEQ ID NO 5
<211> LENGTH: 7
<212> TYPE: PRT
<213> ORGANISM: Rattus norvegicus

<400> SEQUENCE: 5

Phe Ala Ser Gln Ser Ile Ser
1               5

<210> SEQ ID NO 6
<211> LENGTH: 9
<212> TYPE: PRT
<213> ORGANISM: Rattus norvegicus

<400> SEQUENCE: 6

Gln Gln Thr Phe Ser Leu Pro Tyr Thr
1               5
```

```
<210> SEQ ID NO 7
<211> LENGTH: 10
<212> TYPE: PRT
<213> ORGANISM: Artificial Sequence
<220> FEATURE:
<223> OTHER INFORMATION: synthetic peptide

<400> SEQUENCE: 7

Gly Tyr Ile Phe Thr Asp Tyr Ala Met His
1               5                   10

<210> SEQ ID NO 8
<211> LENGTH: 17
<212> TYPE: PRT
<213> ORGANISM: Artificial Sequence
<220> FEATURE:
<223> OTHER INFORMATION: synthetic peptide

<400> SEQUENCE: 8

Thr Phe Ile Pro Leu Leu Asp Thr Ser Asp Tyr Ala Gln Lys Phe Gln
1               5                   10                  15

Gly

<210> SEQ ID NO 9
<211> LENGTH: 11
<212> TYPE: PRT
<213> ORGANISM: Artificial Sequence
<220> FEATURE:
<223> OTHER INFORMATION: synthetic peptide

<400> SEQUENCE: 9

Met Gly Val Thr His Ser Tyr Val Met Asp Ala
1               5                   10

<210> SEQ ID NO 10
<211> LENGTH: 11
<212> TYPE: PRT
<213> ORGANISM: Artificial Sequence
<220> FEATURE:
<223> OTHER INFORMATION: synthetic peptide

<400> SEQUENCE: 10

Arg Ala Ser Gln Pro Ile Ser Ile Ser Val His
1               5                   10

<210> SEQ ID NO 11
<211> LENGTH: 7
<212> TYPE: PRT
<213> ORGANISM: Artificial Sequence
<220> FEATURE:
<223> OTHER INFORMATION: synthetic peptide

<400> SEQUENCE: 11

Phe Ala Ser Gln Ser Ile Ser
1               5

<210> SEQ ID NO 12
<211> LENGTH: 9
<212> TYPE: PRT
<213> ORGANISM: Artificial Sequence
<220> FEATURE:
<223> OTHER INFORMATION: synthetic peptide

<400> SEQUENCE: 12

Gln Gln Thr Phe Ser Leu Pro Tyr Thr
1               5
```

```
<210> SEQ ID NO 13
<211> LENGTH: 107
<212> TYPE: PRT
<213> ORGANISM: Mus musculus

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 14
<211> LENGTH: 120
<212> TYPE: PRT
<213> ORGANISM: Mus musculus

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Ala Met Ser Trp Val Arg Gln Ala Pro Gly Lys Gly Leu Glu Trp Val
        35                  40                  45

Ser Ile Ile Ser Gly Ser Gly Gly Phe Thr Tyr Tyr Ala Asp Ser Val
    50                  55                  60

Lys Gly Arg Phe Thr Ile Ser Arg Asp Asn Ser Arg Thr Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Val Ala Pro Gly Thr Phe Asp Tyr Trp Gly Gln
            100                 105                 110

Gly Ala Leu Val Thr Val Ser Ser
            115                 120
```

PHARMACEUTICAL COMPOSITION FOR AMELIORATING THE SYMPTOMS AND DISEASE OF THE RESPIRATORY INFECTION CAUSED BY HUMAN METAPNEUMOVIRUS (HMPV), WHICH COMPRISES AT LEAST ONE AGENT THAT NEUTRALIZES THE FUNCTION OF TSLP AND/OR TSLPR AND/OR OX40L AND/OR CD177 MOLECULES, AND A PHARMACEUTICALLY ACCEPTABLE EXCIPIENT, AND USE THEREOF

CROSS REFERENCE TO RELATED APPLICATION

This Application is a 371 of PCT/IB2016/052180 filed on Apr. 15, 2016.

FIELD OF THE INVENTION

The present invention relates to a pharmaceutical composition and therapeutic treatment for ameliorating the symptoms and disease of the respiratory infection caused by human Metapneumovirus (hMPV), which comprises antagonists against thymic stromal lymphopoietin (TSLP), against TSLP receptor (TSLPR), OX40 molecule ligand (OX40L) and CD177 molecule (also called HNA-2a, NB1, or PRV-1) expressed in human neutrophils (which is homologous to the Lymphocyte Antigen 6 complex or Ly-6G, which is expressed in murine neutrophils) to be used as a treatment for reducing the symptoms and disease of patients infected with human Metapneumovirus.

BACKGROUND OF THE INVENTION

Human Metapneumovirus (hereinafter, hMPV) is the etiological agent of a representative percentage of hospitalizations and morbidity associated to acute respiratory diseases of the upper and lower respiratory tracts, especially in infants, elderly and immunocompromised individuals. This virus infection is associated to a wide range of pathologies, among which bronchiolitis and pneumonia correspond to conditions that have a greater socio-economic impact. Additionally, hMPV infection has been associated with gastroenteritis and keratoconjunctivitis. For example, Calvo et al. (2008) demonstrated over a period of 3 years that the cumulative incidence of acute respiratory infections caused by respiratory viruses: respiratory syncytial virus (RSV), adenovirus (ADV) and hMPV, are responsible for 64.5% of hospitalizations of children under 2 years, the incidence for each of the viruses being 35.4%, 19.3% and 9.8%, respectively. Production of repeated infections throughout childhood is an interesting feature that hMPV shares with other high incidence respiratory viruses, this phenomenon is possibly associated with a failure to establish a protective immune response against the first infection during the first months of life. There are no studies to date on the specific economic impact caused by hMPV infection, however, the incidence of hospitalization due to hMPV has been estimated at ⅓ of the incidence of hospitalization due to RSV. Studies conducted in developed countries estimate that individual cost of RSV infection is over 3,000 euros ($ 1,860,000 Chilean pesos) with an upper limit of up to 8,400 euros ($ 5,200,000 Chilean pesos). The costs associated to individual hospitalization are approximate and are based on a pathological process of similar characteristics that requires hospitalization.

Although hMPV and hRSV virus are grouped within the *Metapneumovirus* and *Pneumovirus* genus, respectively; hMPV virus is classified in the same family and subfamily in which hRSV is classified, Paramyxoviridae and Pneumovirinae, respectively. hMPV genome comprises a non-segmented, single-stranded, negative-sense ribonucleic acid (ssRNA), so that the viral proteins are arranged in a 3' to 5' direction (according to their sequence) as follows: N, P, M, F, M2 (ORF1 and ORF2), SH, G and L. Nucleocapsid protein N and matrix protein M, together with the transmembrane glycoproteins F, G and SH are responsible for packaging the genetic material and defining the viral particle structure. The other four proteins, M2-1, M2-2, P and L, are involved in viral replication and transcription. There are 2 hMPV subtypes, classified as A and B according to the two antigenic groups they belong, based on sequence differences located mainly in the F and G proteins. Although these proteins present a certain degree of difference, there is a high identity relative to the other proteins encoded by the viral genome. There is currently no vaccine or antiviral treatment available for hMPV, although some candidate vaccines have been developed that could prevent this infection in the future.

HMPV mainly infects airway epithelial cells (AECs) and rapidly induces the destruction of the lung architecture, characterized by an increased thickening of myofibroblasts adjacent to the airways epithelium. The infection continues with detachment of epithelial cells, loss of cell cilia and acute lung inflammation, characterized by abundant perivascular cells infiltrate, moderate peribronchiolar and bronchial cell infiltrates, alveolitis, and mucus production, this condition can lead to patient hospitalization and even, in more extreme cases, to death, especially in the elderly. So it is extremely urgent to have an effective treatment to reduce the destructive inflammatory effects and disease in the lung resulting from an hMPV infection. The only treatment that currently exists for hMPV infections is support treatment and includes supplemental oxygen and hydration, as required. Generally, treatments with corticosteroids and bronchodilators are not useful and are not recommended. Antibiotics are only prescribed to patients with fever, pneumonia, evidenced by chest x-ray examination and clinically suspected of having a bacterial co-infection. At present, there is no antiviral or antibody treatment for effectively ameliorating the symptoms caused by an hMPV infection. In view of this problem, there is a need to provide an alternative for effectively ameliorate the symptoms caused by an hMPV infection, in order to reduce both inflammation and viral replication in the lung of the murine model. In this sense, the present invention provides neutralizing agents such as humanized anti-TSLP, anti-TSLPR (TSLP receptor), anti-OX40L and anti-CD177 neutralizing monoclonal antibodies, as well as any molecule or artifact that neutralizes the function or biological action of said molecules in humans for reducing the symptoms and disease of hMPV-infected patients. Therefore, clinical professionals could to treat early, adequately and efficiently the symptoms and respiratory disease in hMPV-infected patients while preventing more severe complications.

A monoclonal antibody is a type of homogeneous antibody that is characterized by specifically recognizing a single antigen. They are produced by a single hybrid cell (hybridoma), which is the product of the fusion of a B cell clone and a tumor plasma cell. The ability to bind specifically and with high affinity to an antigen has promoted the development of monoclonal antibodies as a very useful tool for detecting molecules of great scientific, clinical and industrial interest. At present, monoclonal antibodies are widely used, both in basic and applied research, because their specificity and reproducibility provides a better support for research. However, biomedicine is the area where monoclonal antibodies have had enormous practical applications, whether for the diagnosis and treatment of multiple infectious diseases, and as therapy for other pathologies. Monoclonal antibodies for therapeutic use have gained great relevance. At present, there are therapeutic treatments for different pathologies through the use of commercial monoclonal antibodies such as: Alemtuzumad, Gemtuzumab Ozogamicin, Rituximab, Trastumab, among others

SUMMARY OF THE INVENTION

The present invention relates to a pharmaceutical composition and therapeutic treatment method which uses said pharmaceutical composition for ameliorating the respiratory infection symptoms and disease caused by human Metapneumovirus (hMPV).

DESCRIPTION OF THE FIGURES

Total RNA from A549 cells exposed to mock, or UV-inactivated hMPV, or hMPV with 0.1 MDI, or hMPV with 1 MDI was analyzed by reverse transcriptase and real-time PCR (qRT-PCR), using specific primers for TSLP (A) and for N-hMPV transcripts (B), after 24 hours. (C and D). In addition, similar samples were analyzed after 12, 24 and 48 hours for induction of TSLP (C) and IL-33 (D) messenger RNAs. 10 μg polyinosinic: polycytidylic acid was included as control. (E and F) Total RNA from A549 cells exposed to mock, or hMPV (E), or RSV (F) with an MDI equal to 1 for each virus, was analyzed by qRT-PCR using specific primers for TSLP, IL-33 and IL-8 after 24 hours. Each well contained $2 \times 10^5$ cells. The plotted data represents the mean±standard deviation of triplicate wells.

On days 1, 3, 6 and 8 post-inoculation, viral RNA and TSLP messenger RNA were measured by qRT-PCR in the lungs of mock-inoculated mice or hMPV-inoculated mice. (C and D) Neutrophils (Gr1$^+$/CD11b$^+$) in bronchoalveolar lavages (BALs) and from dendritic cells (DCs) expressing OX40L$^+$ (OX40L$^+$/IA/I-E$^{high}$ CD11c$^+$ CD11b$^+$) recruited in the lung were analyzed by flow cytometry. Data in the graph represent the percentage of cells with lineage-specific markers. (E) Mean fluorescence intensity of OX40L in IA/I-E$^{high}$ CD11c$^+$ CD11b$^+$ DCs were also measured in the lungs of hMPV-infected mice compared to uninfected mice 6 days post-infection. The data represent the mean±standard deviation of two independent experiments with 3 or 4 mice per group. *p<0.05; **p<0.01; measured by Student's t-test and one-way or two-way ANOVA.

Groups of wild type (WT) BALB/c mice and TSLPR-deficient mice (tslpr−/−) were intranasally inoculated with either mock or 1×10$^6$ PFU of hMPV. Then, body weight loss of each experimental group was recorded until day 8. (A) Body weight is expressed as a percentage from the base line weight without treatment. (B) BALs of both experimental groups after 4 days of infection were collected and analyzed by flow cytometry. Data in the graph represent the percentage of Nuclear Polymorphs (Gr1$^+$/CD11b$^+$) in BALs of mock-inoculated or hMPV-inoculated tslpr$^{-/-}$ and WT mice. (C) H&E Staining of lung tissue from mice of each of the experimental groups in each day. (D) Cell infiltration in alveoli and peribronchial tissues was observed and measured through histopathological evaluation using a double blind strategy. (E) The number of neutrophils in the walls and alveolar spaces were counted in high power fields of a total of 5 images for each animal. Images were acquired with a 40× magnification (scale bar=100 μm). (F) 1, 3, 4, 6 and 8 days post-infection, lung homogenates from WT mice and tslpr$^{-/-}$ from each experimental group were collected and viral RNA was measured by qRT-PCR, using specific primers for the hMPV N gene. The data represent the mean±standard deviation of three independent experiments with 3 or 4 mice per group. p>0.05=ns, *p<0.05; p<0.01; *p<0.001; measured by Student's t-test and one-way or two-way ANOVA.

Groups of WT and tslpr$^{-/-}$ mice were intranasally inoculated with either mock or 1×10$^6$ PFU of hMPV. (A-G) After 4 days post-infection, lungs of both experimental groups were collected and the cellular populations of the innate and adaptive immune response were analyzed by flow cytometry with lineage-specific markers. Plotted data represent the absolute numbers of each analyzed cell population in the lungs of mock- or hMPV-inoculated tslpr$^{-/-}$ and WT mice. (H-K) 4 days post-infection, LABs and lungs from the experimental groups were collected and the CD8$^+$ and CD4$^+$ T cells were analyzed by flow cytometry with lineage-specific markers. Plotted data represent absolute numbers of each analyzed cell population in BALs (H and I) or lungs (J and K). The data represent the mean±standard deviation of an independent experiment with 4 mice per group. p>0.05=ns, *p<0.05; **p<0.01; measured by Student's t-test.

Groups of tslpr$^{-/-}$ and WT BALB/c mice were intranasally inoculated with either mock or 1×10$^6$ PFU of hMPV, and lungs from both experimental groups were collected after 4 days post-infection. CD4$^+$ and CD8α$^+$ T cells were analyzed by flow cytometry with lineage-specific markers and intracellular staining for IFN-γ, TNF-α, IL-4, IL-10 IL-12, and IL-13. Graph data are the percentage of each subset of T cells producing the specific cytokines analyzed in mock- or hMPV-inoculated tslpr$^{-/-}$ and WT mice. (C and D) 4 and 6 days post-infection, lung homogenates from WT and tslpr$^{-/-}$ mice of each experimental group were collected and viral RNA was quantified by qRT-PCR, using specific primers for IL-4, IL-13, IFN-γ, IL-5, IL-10 murine cytokines and TNF-α genes. (E) 1, 3, 6 and 8 days post-infection, lung homogenates from the mice of each experimental group were collected and viral RNA was quantified by qRT-PCR, using specific primers for TARC/CCL17 gene. * on each bar represent the significant value relative to base lines derived from mock-inoculated mice. The data represent the mean±standard deviation of one (A and B), three (C and D)

and two (E) independent experiment(s) with 4 mice per group. p>0.05=ns, *p<0.05; **p<0.01; measured by Student's t-test.

Groups of BALB/c mice were intraperitoneally treated with PBS or with 150 μg anti-TSLP or with 150 μg anti-OX40L, or 150 μg of isotype control antibodies. Twenty-four hours later, these groups of mice were intranasally inoculated with either mock or $0.5 \times 10^6$ PFU of hMPV and additionally treated again with 50 μg of the corresponding antibodies, previously mentioned. (A and B) Graph data represent the percentage of polymorphonuclears (PMN, Gr1$^+$/CD11b$^+$) analyzed in LABs of each experimental group at 3 and 6 days post-infection. (C and D) At 3 and 6 days post-inoculation, lung homogenates from mice of each experimental group were collected and viral RNA was quantified by qRT-PCR, using specific primers for hMPV-N gene. (E-F) In addition, at day 6 post-inoculation, a lung portion from mice of each experimental group was fixed with H&E. The images were acquired at a 40× and 10× magnification (scale bar=50 and 200 μm, respectively). (G) Images obtained for each sample were double-blind evaluated for histopathology. (H) At day 6 post-inoculation, mediastinal lymph nodes from each of the experimental groups were collected and the frequency of DCs expressing OX40L was analyzed by flow cytometry. (I and J) The numbers of neutrophils in the peribronchial areas, in walls and alveolar spaces were counted in high power fields. The data represent the mean±standard deviation from two independent experiments with 3 mice per group. p>0.05=ns, *p<0.05; ***p<0.001; measured by Student's t-test and one-way or two-way ANOVA.

Groups of tslpr$^{-/-}$ and WT BALB/c mice were treated either with isotype control antibody (IgG2a) or anti-Ly6G antibody. These treated mice were intranasally inoculated with either mock or $1 \times 10^6$ PFU hMPV, and 4 days post-infection, a portion of mouse lung tissue from each experimental group was fixed, prepared and stained with H&E. Cell infiltration in alveolar and peribronchial tissues was observed and evaluated for histopathologic score (A) Images obtained from each sample were double-blind evaluated for histopathology, using the following criteria: 0, no cellular infiltration; 1, minimal cellular infiltration; 2, mild cellular infiltration; 3, moderate cellular infiltration; and 4, severe cellular infiltration. Moreover, the number of neutrophils on walls and alveolar spaces (B) and peribronchials areas (C) was also counted in high power fields, in a total of 5 images per animal. Images of lung slices were obtained using an inverted microscope (CKX41, Olympus) and an Infinity 2 Lumenerata camera. In addition, the viral RNA was quantified in the lungs of each experimental group by qRT-PCR, using the specific primers for the hMPV-N gene (D). The data represent mean±standard deviation of an independent experiment with 3 or 4 mice per group. p>0.05=ns, *p<0.05; p<0.01; *p<0.001; measured by Student's t-test and one-way or two-way ANOVA.

DETAILED DESCRIPTION OF THE INVENTION

In a first aspect, the present invention considers a pharmaceutical composition for ameliorating the respiratory infection symptoms and disease caused by human Metapneumovirus (hMPV). In particular, said pharmaceutical composition comprises at least one agent or antagonist that neutralize or inhibit the function of TSLP, TSLP receptor (TSLPR), OX40L and/or CD177 molecules and a pharmaceutically acceptable excipient. In a particular embodiment, the antagonists that neutralize the function of TSLP and/or TSLPR and/or OX40L, and/or CD177 molecules may be monoclonal antibodies, biological or synthetic molecules. In a particular embodiment, the pharmaceutically acceptable excipient is water.

In a particular embodiment of the pharmaceutical composition of the invention, the antagonists that neutralize the function of the TSLP, TSLPR, OX40L, and/or CD177 molecules comprise anti-human TSLP, anti-human TSLPR, anti-human OX40L and anti-CD177 monoclonal antibodies and that neutralize the function of TSLP, TSLPR, OX40L molecule and CD177 molecule, present in neutrophils, respectively.

In a particular embodiment of the pharmaceutical composition of the invention, the anti-human TSLP monoclonal antibodies being used are selected from: AMG 157 monoclonal antibody (found in clinical trial with identification number NCT02237196); or the antibody defined by its 3 heavy chain CDRs in the sequences SEQ ID NO: 1, 2 and 3, and the 3 light chain CDRs in the sequences SEQ ID NO: 4, 5, 6; or the antibody defined by the 3 heavy chain CDRs in the sequences SEQ ID NO: 7, 8 and 9, and the 3 light chain CDRs in the sequences SEQ ID NO: 10, 11, 12. The invention is not limited to these antibodies, which correspond to one embodiment, but it is being described for any anti-human TSLP monoclonal antibody.

In a particular embodiment of the pharmaceutical composition of the invention, the anti-human OX40L monoclonal antibodies used are selected from: huMAb OX40L monoclonal antibody (is in clinical trial with identification number NCT00983658); or the antibody defined by the light chain variable domain having the amino acid sequence defined by SEQ ID NO: 13, and the heavy chain variable domain having the amino acid sequence defined by SEQ ID NO: 14. In a preferred embodiment of the invention, the light chain of the antibody has at least 80% identity with SEQ ID NO: 13, at least 85%, 90%, 95%, 99% identity. On the other hand, the antibody heavy chain has at least 80% identity with SEQ ID NO: 14, at least 85%, 90%, 95%, 99% identity. The invention is not limited to these antibodies, which correspond to one embodiment, but it is being described for any anti-human OX40L monoclonal antibody.

In a particular embodiment of the pharmaceutical composition of the invention, the anti-human CD177 monoclonal antibodies used are selected from commercial antibodies such as: Purified anti-human CD177 (catalog number 315802, clone MEM-166, Biolegend®); Purified anti-human CD177 (catalog number 14-1779-82, clone MEM-166, eBioscience); Anti-CD177 antibody (catalog number ab8092, clone MEM-166, Abcam); Rabbit Polyclonal anti-CD177 (catalog number H00057126-D01P, Novus Biologicals); anti-CD177 antibody (catalog number orb247491, Biorbyt); mouse anti-human CD177 (catalog number MCA2045, clone MEM-166, Absortec); Anti-CD177 (catalog number LS-C78885, LSBio); Rabbit anti-Human CD177 Polyclonal Antibody (catalog numberMBS9414089, MyBiosource); CD177 Monoclonal antibody (catalog number MA1-19250, clone MEM-166, Thermofischer Scientific). The invention is not limited to these antibodies, which correspond to one embodiment, but it is being described for any anti-human CD177 monoclonal antibody.

Another embodiment of the pharmaceutical composition of the invention consider biological or synthetic molecules that inhibit the function of each one of TSLP, TSLPR, OX40L, and CD177 molecules.

Antagonists that inhibit the function of each one of TSLP, TSLPR, OX40L, and CD177 molecules can be used for the treatment of symptoms and disease in hMPV-infected patients, specifically by reducing inflammation and viral replication in the lungs.

Figure 1:
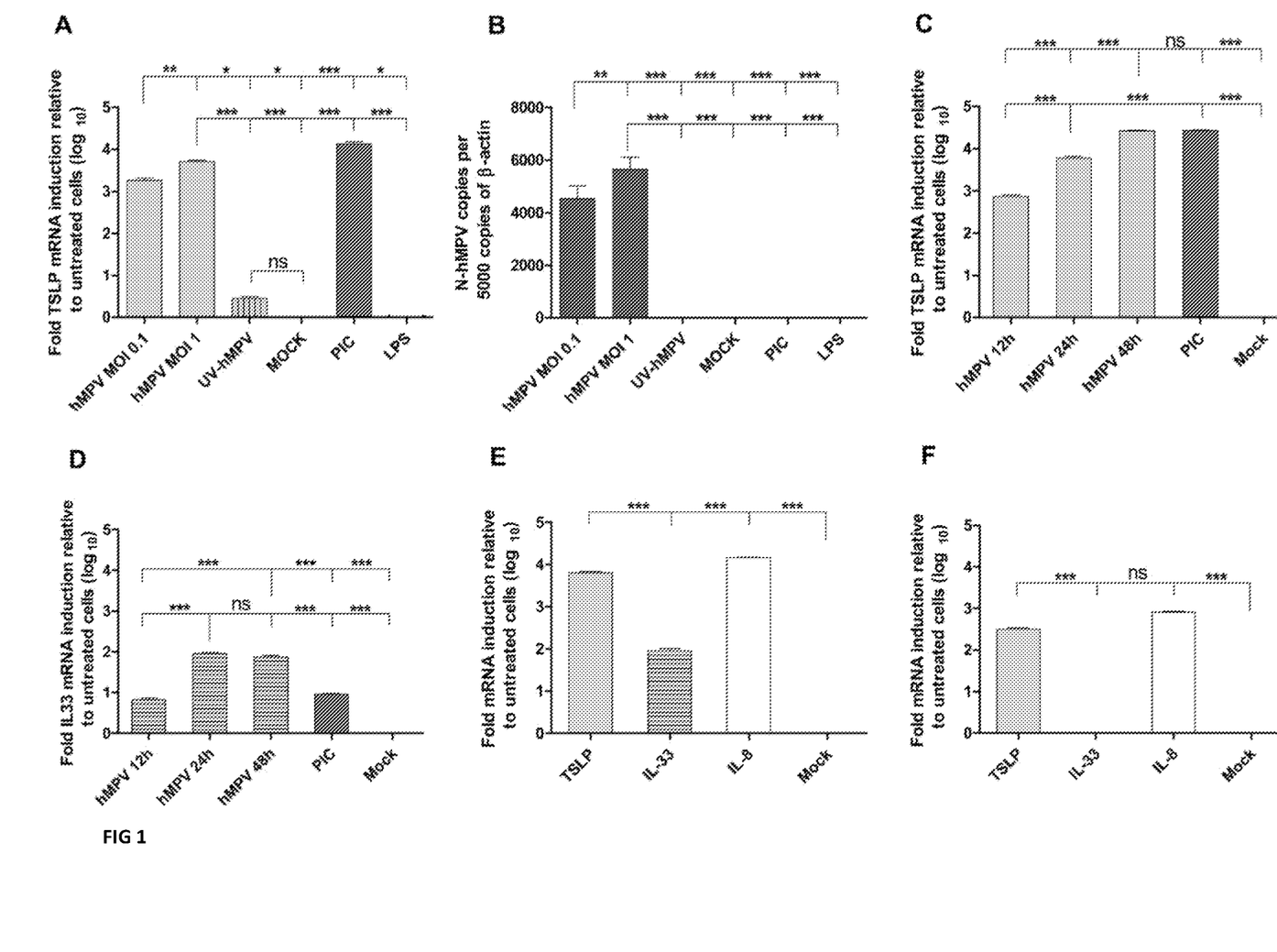
FIG. 1: Human alveolar epithelial cells (A549) infected with hMPV induce TSLP and IL-33 expression.
Figure 2:
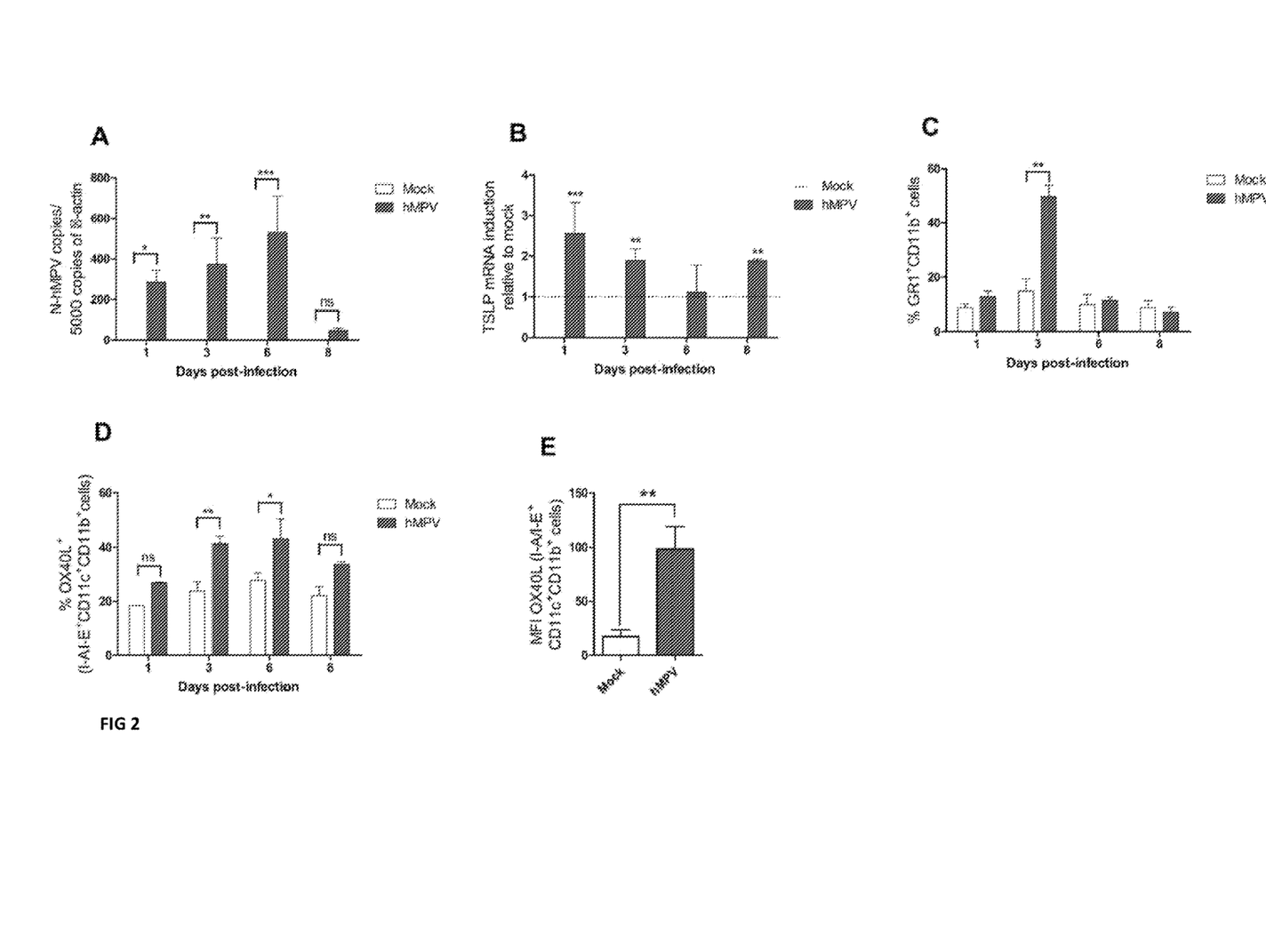
FIG. 2. HMPV induces lung infiltration of OX40L$^+$/I-A/I-E$^{high}$ CD11c$^+$ CD11b$^+$ cells. (A and B) Groups of BALB/c mice (albino mouse, inbred laboratory strain) were intranasally inoculated with either mock or hMPV.
Figure 3:
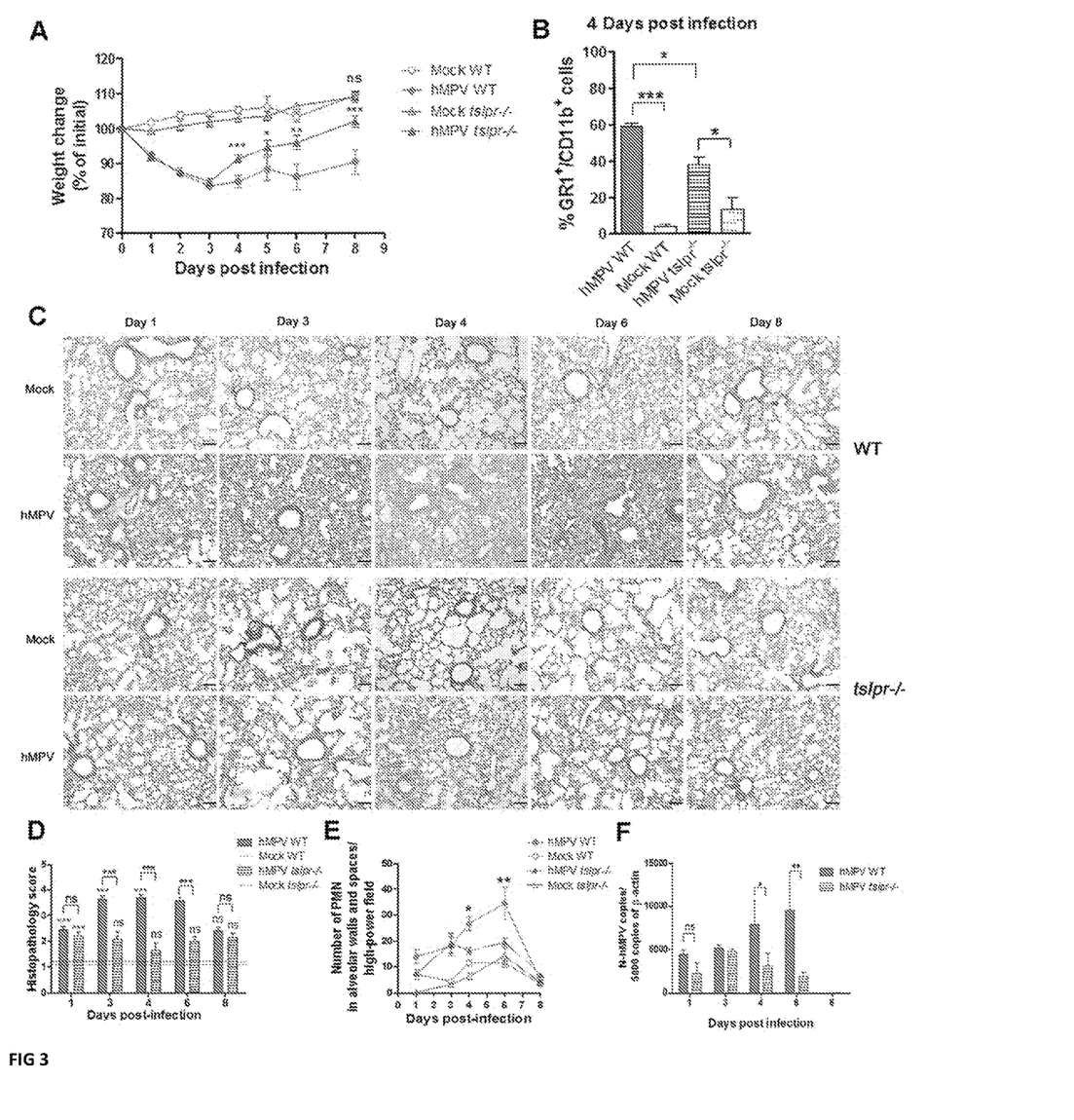
FIG. 3. Functional lack of TSLP pathway aids weight recovery and prevents lung inflammation in hMPV-infected mice.

In a particular embodiment, the pharmaceutical composition of the present invention comprises at least one antagonist that inhibits the function of at least one of TSLP, TSLPR, OX40L or CD177 molecules. In another embodiment, the pharmaceutical composition of the present invention comprises more than one antagonist that inhibits the function of TSLP, TSLPR, OX40L or CD177 molecules, wherein each one of the agents is directed to inhibit a specific molecule selected from TSLP, TSLPR, OX40L, or CD177.

The present invention has also demonstrated for the first time that the treatment with anti-TSLP or anti-OX40L or anti-Ly6G monoclonal antibodies and/or the lack of TSLPR, wherein anti-Ly6G (in mice) is homologous to anti-CD177 in humans, significantly reduces both inflammation and replication in the lungs during an hMPV infection.

A second aspect of the invention, considers a method of therapeutic treatment which uses the pharmaceutical composition to ameliorate the respiratory infection symptoms and disease caused by the human Metapneumovirus (hMPV). A treatment is designed from antagonists that inhibit the function of TSLP, TSLPR, OX40L or CD177 molecules, particularly where the antagonists are humanized monoclonal antibodies, using each of these monoclonal antibodies, separately or together, simultaneously, in all possible combinations for treating hMPV-infected patients. In addition, it may include different administration regimens, both in concentrations and appropriate times, either intranasally, orally, intravenously or intraperitoneally, so the hMPV-infected patient may undergone a reduction in the disease symptoms and not experience side effects from the treatment. All of those embodiments are within the scope of the present invention.

A third aspect of the invention describes the use of the pharmaceutical composition comprising at least one neutralizing humanized monoclonal antibody or molecules that neutralize the function of TSLP and/or TSLPR and/or OX40L and/or CD177 molecules, to prepare a medicament for treating or ameliorating the symptoms and disease of patients infected with human Metapneumovirus (hMPV).

A fourth aspect of the invention describes the use of at least one humanized monoclonal antibody or neutralizing molecules that neutralize the function of TSLP and/or TSLPR and/or OX40L and/or CD177 molecules (anti-TSLP, anti-TSLPR, anti-OX40L, anti-CD177, respectively), to prepare a medicament for treating or ameliorating the symptoms and disease of patients infected with human Metapneumovirus (hMPV).

Embodiments of the invention, based on tests conducted, are described below, which demonstrate specific characteristics of the invention, however, these descriptions should be understood as exemplary, and not limitations to the scope of the invention.

In particular, as shown in FIGS. 6 and 7, these antibodies are specific for both reducing the inflammatory cell infiltration and improving the histopathological evaluation of the lungs and, for further reducing the viral load in the lungs of hMPV-infected mice, since those mice treated with control isotype do not achieve these effects.

As shown by FIGS. 1 A-F, TSLP and IL-33 expression in human alveolar epithelial cells (A549 cells) was determined using total RNA analysis by quantitative reverse transcription PCR (qRT-PCR), compared to uninfected cells (Mock) and RSV. As a result, the TSLP expression was significantly increased in hMPV-infected A549 cells, as did SRV in a previously published work, but not in mock-inoculated cells. In addition, hMPV induced the expression of IL-33, another cytokine related to the induction of allergic inflammation derived from the epithelium, in these cells but SRV did not.

To determine whether TSLP pathway is activated in the lungs after hMPV infection in an in vivo model, first the expression of TSLP in the lungs of wild type (WT) BALB/c mice was evaluated, as well as the OX40L expression in dendritic cells (DCs, CD11c+/CD11b+) in the lungs. As shown in FIG. 2A-E, hMPV induces increased expression levels of TSLP and the percentage of OX40L-expressing DCs in the lungs of BALB/c mice are consistent with lung inflammation and active viral replication.

In addition, to determine if TSLP pathway contributes to the immunopathology caused by hMPV infection, TSLPR-deficient (tslpr$^{-/-}$) and WT BALB/c mice were intranasally inoculated with either mock or hMPV. Daily weight loss of each experimental group was recorded until day 8. Both hMPV-infected WT mice and tslpr−/− mice were observed to have a significant body weight loss from day 1 to 3 (FIG. 3A). However, an important recovery in body weight was observed in the tslpr$^{-/-}$ mice and not in the WT mice at day 4 post infection (FIG. 3A). In addition, WT mice at day 8 still showed significant weight loss due to hMPV infection while hMPV-infected tslpr−/− mice regained their initial weight (FIG. 3A). Inflammatory cell infiltration was also measured as the percentage of polymorphonuclears (PMN, Gr1$^{+}$/CD11b$^{+}$) in bronchoalveolar lavages (BALs) of both experimental groups at 4 days post-infection, analyzed by flow cytometry. Results showed significantly lower recruitment of Gr1$^{+}$/CD11b$^{+}$ cells in BALs of tslpr$^{-/-}$ mice compared to BALs of WT mice (FIG. 3B). These data were consistent with pulmonary histopathology analyses using H&E staining, where the lungs of hMPV-infected tslpr−/− mice showed an appreciable reduction in cellular infiltration in the alveolar and peribronchial areas, especially on days 4 and 6, compared to lungs of the hMPV-infected WT mice (FIG. 3C). Likewise, the histopathologic score of these samples revealed a significant reduction of lung cell infiltration in hMPV-infected tslpr−/− mice, in comparison with those observed in the lungs of infected WT mice after 3, 4, and 6 days (FIG. 3D). A greater quantification of inflammatory cell infiltrate, involving the interstitial/intra-alveolar areas, showed a significantly lower number of PMN in hMPV-infected tslpr−/− mice, in comparison with those observed in the lungs of infected WT mice at 3, 4, and 6 days (FIG. 3E). These results show that the lack of a functional TSLP pathway significantly reduces the lung inflammation and disease in hMPV-infected mice. Furthermore, to determine if TSLP pathway contributes to replication of hMPV in the respiratory tract, a lung section of hMPV- or mock-inoculated WT and tslpr−/− mice, was collected from each euthanized animal on the days indicated above. Viral loads were quantified by qRT-PCR, using primers targeting the hMPV N-gene. Surprisingly, viral N-gene RNAs were observed to be significantly reduced in hMPV-infected tslpr−/− mice compared with those observed in the lungs of infected WT mice, specifically on days 4 and 6 (FIG. 3F). These findings demonstrate that mice lacking TSLPR have reduced susceptibility to hMPV infection in the airways or limited viral replication. Therefore, FIGS. 3 A-F show: a) an improvement in both the recovery of disease symptoms, such as body weight; b) a significant reduction of inflammatory cell infiltration; c) and viral replication in the lungs of mice lacking TSLPR and infected with hMPV.

Figure 4:
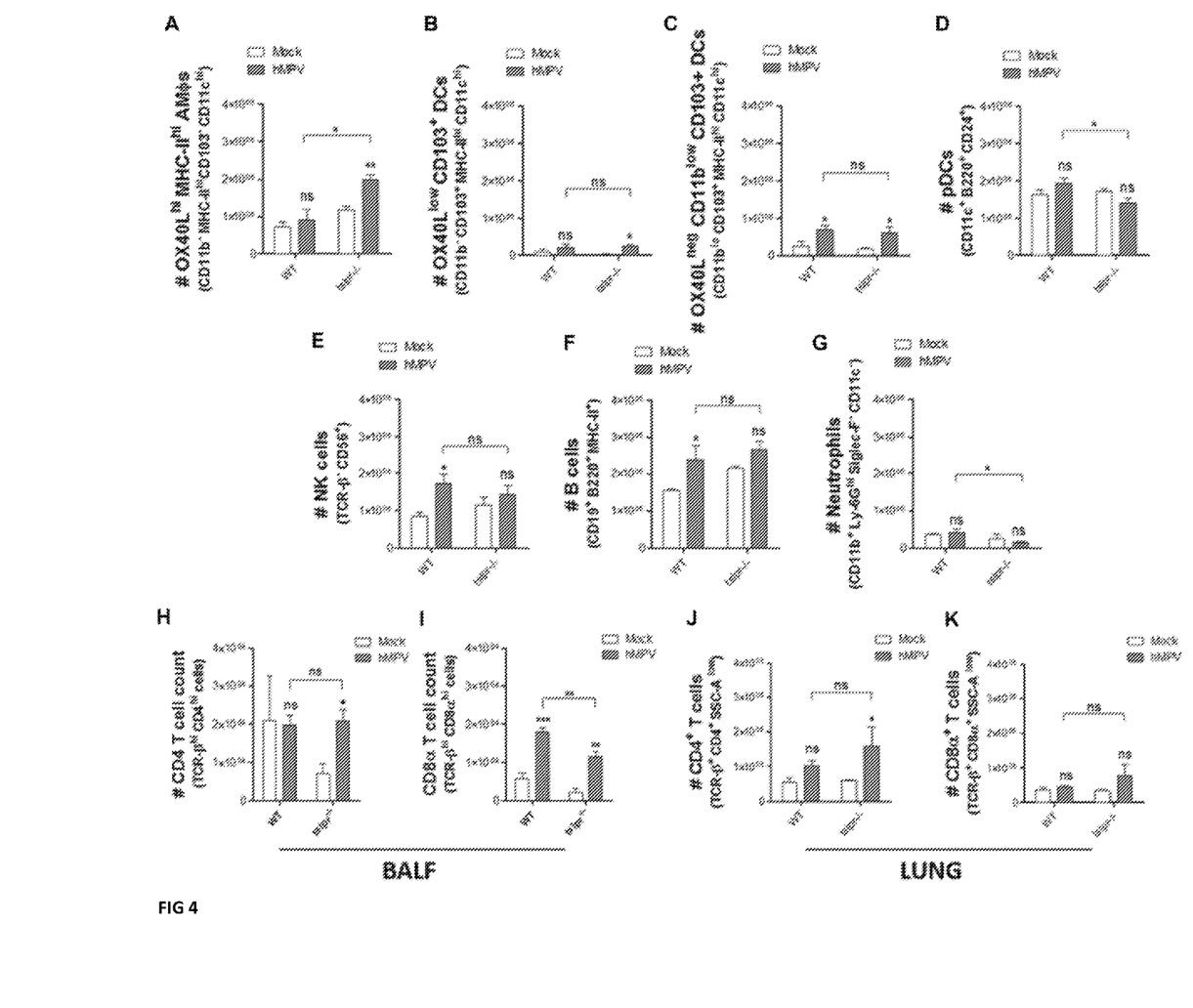
FIG. 4. Functional deficiency of TSLP pathway induces an increase in the frequency of alveolar macrophages expressing OX40L$^+$, CD103$^+$ DCs and CD8α$^+$ and CD4 T cells in BALs and lungs of tslpr$^{-/-}$ mice.

To further elucidate the mechanism explaining the reduced damage and viral replication in mice lacking TSLPR, a detailed analysis of innate and adaptive cell population in lungs of hMPV-infected tslpr$^{-/-}$ and WT mice was carried out by flow cytometry. From these two experimental groups, it was seen: a) higher plasmacytoid dendritic cells (pDCs) and neutrophil infiltration in the lungs of WT mice compared to those of tslpr$^{-/-}$ mice, during hMPV infection; and b) a higher CD4$^+$ and CD8a$^+$ T cells infiltration and alveolar macrophages that express OX40L$^+$ molecule in the lungs of tslpr$^{-/-}$ mice compared to those of WT mice, during hMPV infection (FIGS. 4 A-K). These results suggest that a greater recruitment and activation of CD4$^+$ and CD8a$^+$ T cells in lungs of tslpr$^{-/-}$ mice compared to those of WT mice, can induce a more efficient elimination of the virus in these mice after hMPV infection.

Figure 5:
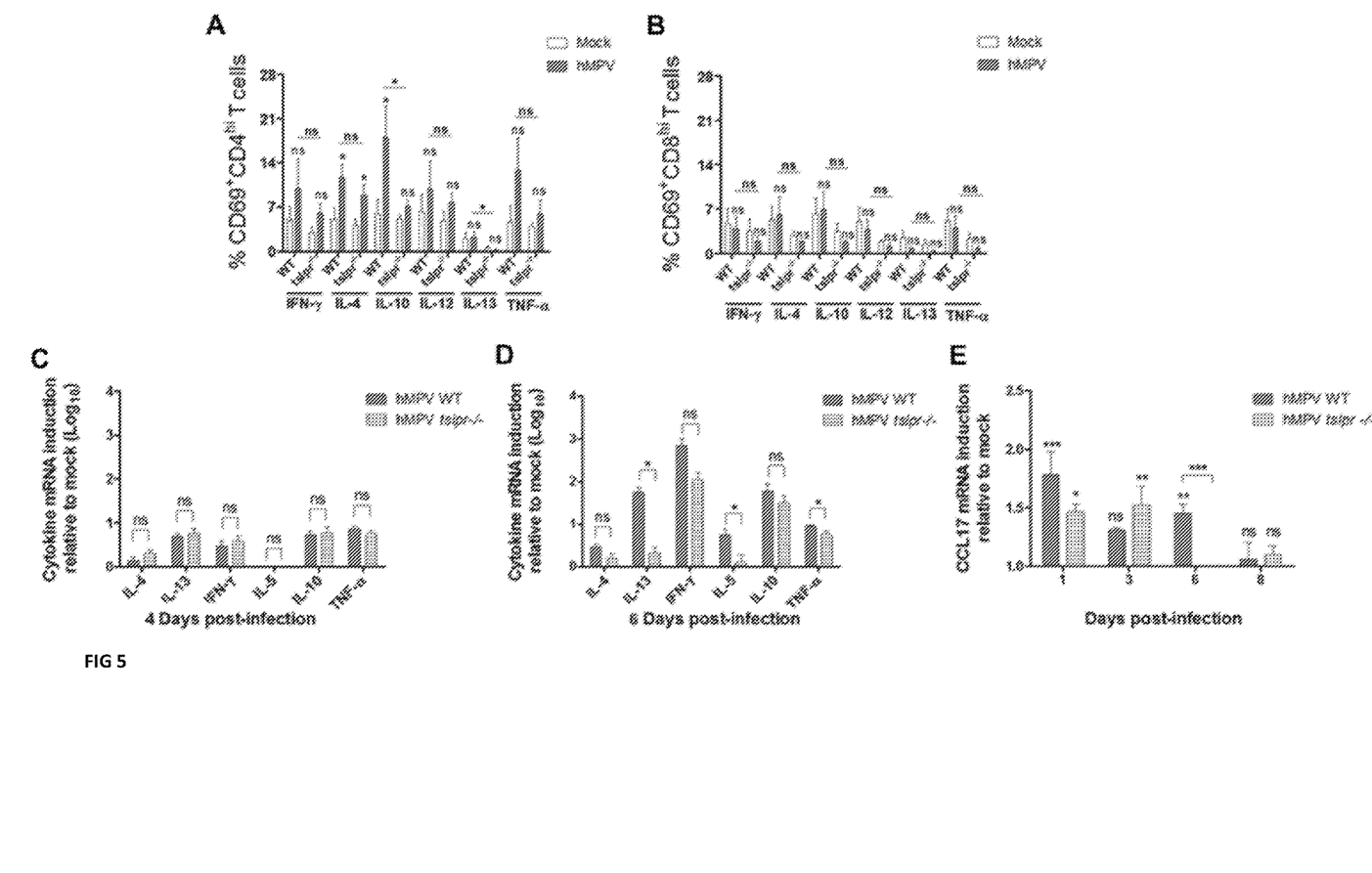
FIG. 5. TSLPR deficiency suppresses the induction of IL-10 and IL-13 producing T cells and damages the sustained expression of IL-5, IL-13 and TNF-α and TARC/CCL17 in lungs after hMPV infection.

In order to better characterize the immune environment defined by the absence of TSLPR and its influence on pulmonary pathogenesis, the phenotype of CD4$^+$ and CD8a$^+$ T cells populations was evaluated by intracellular flow cytometry analysis. These analyzes include intracellular IFN-γ staining for TNF-α, IL-4, IL-10 IL-12 and IL-13 in these two T cells populations. The results of this analysis showed that TSLPR deficiency decreases the induction of IL-10 and IL-13 produced by T cells and impairs the sustained expression of IL-5, IL-13, TNF-α, and TARC/CCL17, mediators involved in inflammatory processes in these mice lungs, after hMPV infection (5A-E). These results demonstrate that TSLP pathway modulates the secretion of various inflammatory mediators, including IL-5, IL-13, and TARC/CCL17, which are related to a Th2- and TNF-α-type response, which is related to Th1-type response.

Figure 6:
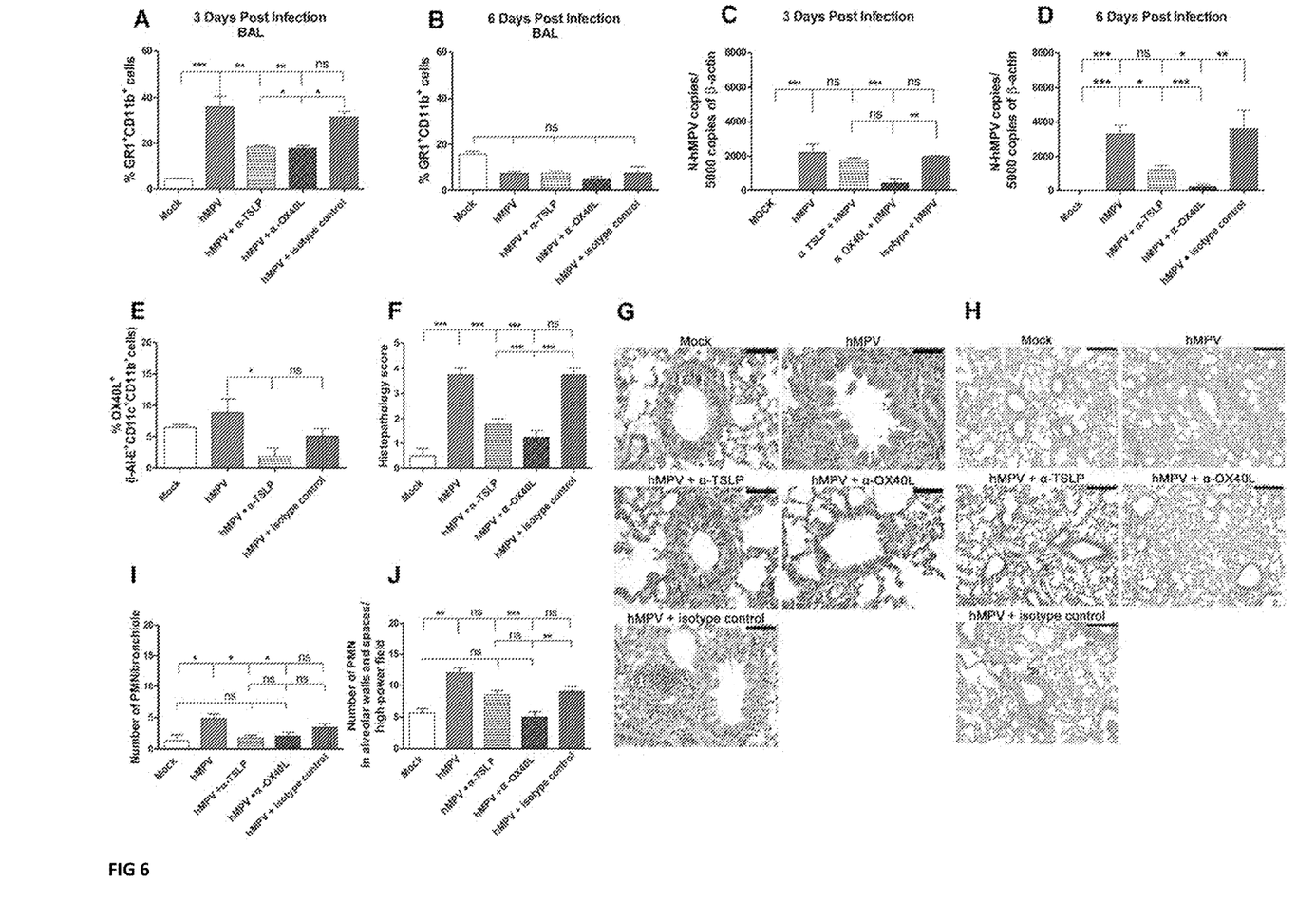
FIG. 6. Treatment with anti-TSLP and anti-OX40L neutralizing antibodies reduces lung inflammation, hMPV viral replication and recruitment of OX40L$^+$ DCs in mediastinal lymph nodes.

To further elucidate the contribution of TSLP pathway to inflammation and viral replication in lungs after hMPV infection, TSLP and OX40L molecules were blocked before the onset of disease using neutralizing antibodies. 24 h before and at the time of hMPV infection, mice were injected with 150 μg and 50 μg of anti-TSLP or anti-OX40L, respectively. PBS and isotype antibody control were included in all experiments. Notoriously, the effect of the antibodies against OX40L and TSLP decreased PMN recruitment in BALs and viral replication in the lungs of infected mice. As shown by FIG. 6A, blocking TSLP/OX40L pathway on day 3 resulted in a significant reduction of neutrophil recruitment in the airways compared to not-treated controls infected by hMPV. On day 6, all groups of animals resolved neutrophil infiltration (FIG. 6B). Regarding the measurements of the viral load, a significant reduction in hMPV N-gene RNA levels was seen in the lungs of mice receiving anti-OX40L treatment, both on day 3 and 6 (FIGS. 6C and D). However, a significant reduction in viral load was only seen on day 6 in mice that have received the anti-TSLP treatment. These results confirm the results obtained with mice lacking TSLPR and demonstrate that blocking TSLP/OX40L pathway components, especially OX40L molecule, promotes more efficient removal of hMPV from lungs of infected mice.

It was also analyzed whether treatments that blocks TSLP pathway modulate recruitment of DCs expressing OX40L in the mesenteric lymphatic nodes (MLN) and lung pathology after hMPV infection. The a flow cytometry analysis was conducted on day 6 to measure the frequency of the DCs expressing OX40L$^+$/CD11b$^+$ in the MLN of anti-TSLP treated and not-treated mice infected with hMPV or isotype control (FIG. 6E). As a result, a significant reduction was observed in the percentage of DCs expressing OX40L$^+$/CD11b+ in the lung MLNs of hMPV-infected mice treated with anti-TSLP compared to infected control animals (FIG. 6E). These data show that TSLPR blocking reduces the recruitment of DCs expressing OX40L$^+$/CD11b$^+$ to the MLN, after an hMPV infection Moreover, a reduced histopathologic score was obtained in the lungs of hMPV-infected mice treated with neutralizing antibodies against any of TSLP or OX40L molecules (FIG. 6F). Consistently, histopathology analysis on day 6 showed that blocking any of TSLP or OX40L molecules significantly reduced immune cell infiltration to peribronchial area, alveolar area and lung interstitium, suggesting a decrease in lung parenchyma inflammation (FIGS. 6 G-H).

PMN amount was also measured in the inflammatory infiltrates involving the peribronchial areas (peribronchiolitis) (FIG. 6I) and interstitial/intra-alveolar areas (interstitial pneumonitis/alveolitis) (FIG. 6J). As a result, a significant reduction in PMN infiltration was achieved in both lung areas of mice receiving anti-OX40L treatment, but those receiving anti-TSLP treatment which were infected with hMPV achieve a significant reduction only in the peribronchial area (FIGS. 6I and J).

These findings demonstrate that treatment with both anti-TSLP and anti-OX40L antibodies also reduce both lung inflammation, with a significant decrease of inflammatory cell infiltration, and viral replication in the lungs after hMPV infection, using the murine model.

Figure 7:
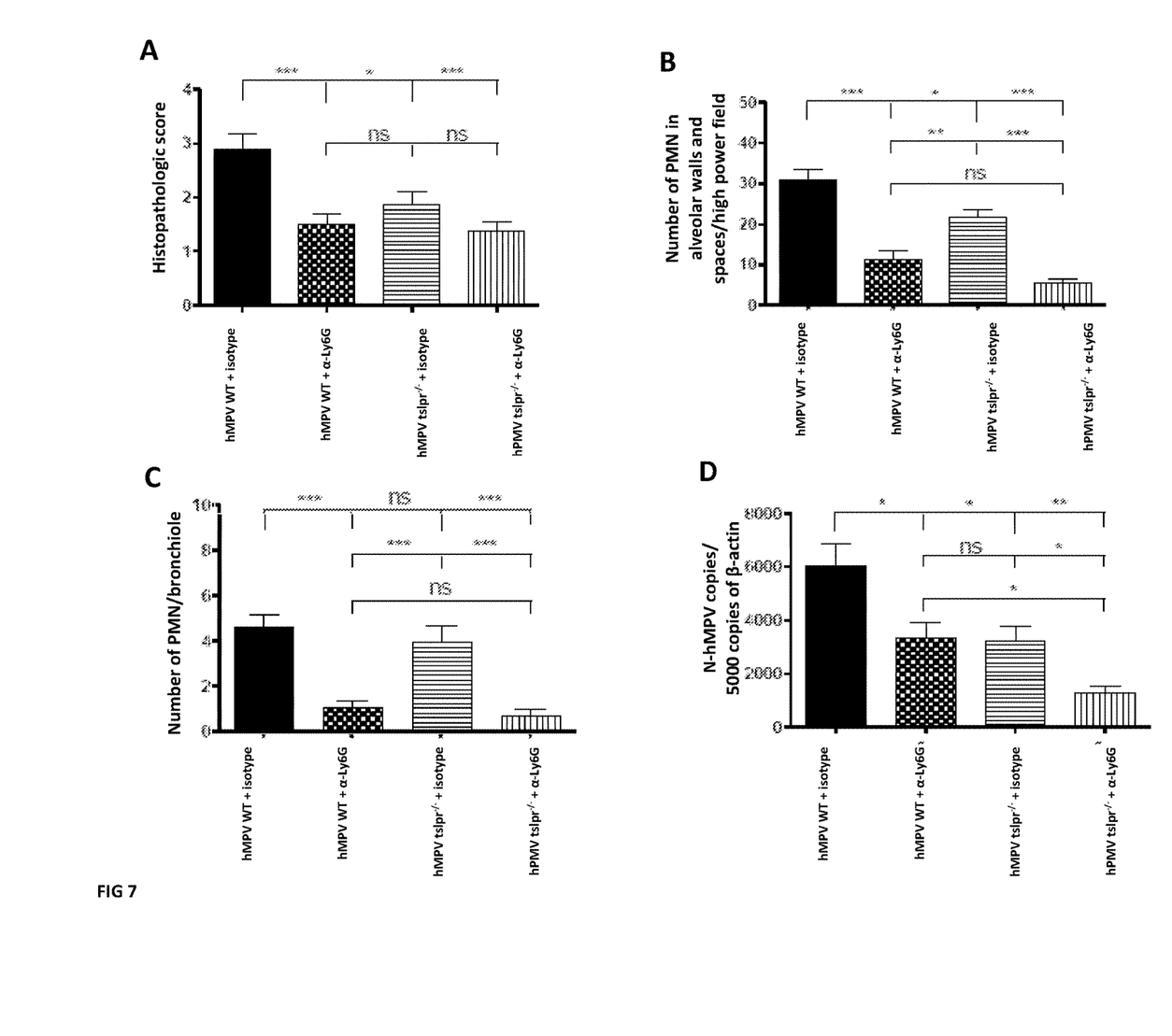
FIG. 7. Treatment with anti-Ly6G reduces inflammation and hMPV replication in lungs of wild type (WT) BALB/c and TSLPR-deficient (tslpr−/−) mice, after hMPV infection.

To further elucidate the mechanism explaining the reduction of lung damage and viral replication in the absence of TSLPR after hMPV infection in mice, the role of neutrophils in the hMPV infection pathogenesis was evaluated in both groups of WT and tslpr$^{-/-}$ mice. For this, WT and tslpr$^{-/-}$ mice (both of BALB/c strain) groups were intraperitoneally treated with anti-Ly6G antibodies or isotype control. As a result, a significant reduction of neutrophils in the blood, LAB s and lungs of both WT and tslpr$^{-/-}$ mice treated with anti-Ly6G was obtained, but not in those treated with isotype control, this indicate that neutrophil depletion occurred in an efficient and an specific way. Lung inflammation was then analyzed by making histopathologic score studies and quantifying the number of neutrophils infiltrated into the lung tissue, involving both peribronchial areas (peribronchiolitis) and interstitial/intra-alveolar areas (interstitial pneumonitis/alveolitis). Administration of anti-Ly6G antibody in both groups of hMPV-infected mice resulted in a significant reduction in the histopathologic score for WT mice, similar to those levels obtained for tslpr$^{-/-}$ mice, which was also reduced, when compared to those treated with isotype control antibody (FIG. 7 A), demonstrating that neutrophil depletion in hMPV-infected WT mice reduces inflammation and lung damage. In addition, the number of neutrophils in both alveolar spaces and its walls and bronchioles was significantly lower in hMPV-infected WT and tslpr$^{-/-}$ mice treated with the anti-Ly6G antibody, compared to those treated with isotype control antibody (FIGS. 7 B and C). These data show that neutrophils in hMPV-infected mice contribute to induce inflammation and lung damage and lack of TSLPR would contribute in reducing the presence of neutrophils, but not absolutely. The role of neutrophils in viral replication in the lungs of hMPV-infected WT and tslpr$^{-/-}$ mice was evaluated by qRT-PCR measuring viral load in the lungs of hMPV-infected WT and tslpr$^{-/-}$ mice treated with anti-Ly6G or isotype control antibodies. Surprisingly, a significant reduction of viral RNA copies was seen in the lungs of hMPV-infected WT mice treated with anti-Ly6G antibody compared to those treated with isotype control, which reached levels similar to infected tslpr$^{-/-}$ mice treated with isotype control antibody (FIG. 7 D). In addition, a higher reduction in viral load was seen in infected tslpr$^{-/-}$ mice treated with anti-Ly6G antibody, compared with HMPV-infected WT mice treated with anti-Ly6G antibody. These results demonstrate that the recruitment of neutrophils in the airways, which also depends on TSLP pathway, is contributing to viral replication in the lungs of hMPV-infected mice. In conclusion, FIGS. 7 A-D show that the method with the neutralizing antibody against mouse Ly-6G, present in neutrophils and which is the molecule homologous to CD177 in humans, significantly reduces both inflammatory cell infiltration and viral replication in the lungs of hMPV-infected mice. This invention considers the use of these antibodies or inhibitory molecules, both individually and together, simultaneously, in all combinations, to increase the neutralizing effect on inflammation and hMPV replication in the lungs. For example, FIGS. 7 B and D show the synergistic effect between the functional lack of TSLPR and the anti-Ly6G decreases more efficiently inflammation and hMPV replication in the lungs of mice, used as an animal model, than the separate blockage of these pathways. These antibodies or inhibitory molecules, for each one of the aforementioned molecules, can be applied either intravenously, intranasally, orally or intraperitonially to patients suffering from a respiratory infection due to hMPV, duly diagnosed by a treating physician.

EXAMPLES OF APPLICATION

Below are described examples that demonstrate the protective effect of using the monoclonal antibodies of the invention.

Example 1

Assay of the Protective Effect of Treatment with Anti-TSLP or Anti-OX40L Neutralizing Antibodies in Reducing Lung Inflammation and hMPV Viral Replication This test is directed to evaluate the protective effect of anti-TSLP and anti-OX40L neutralizing monoclonal antibodies in reducing pulmonary inflammation and hMPV viral replication, groups of BALB/c mice were intraperitoneally treated with PBS or with 150 µg anti-TSLP (Anti-Mouse TSLP Functional Grade Purified, catalog number 16-5491-85, from eBioscience), or with 150 µg anti-OX40L (LEAF® Purified anti-mouse CD252, catalog number 108808, from Biolegend®), or with 150 µg control isotype antibodies. Twenty-four hours later, these groups of mice were intranasally inoculated either with mock or $0.5 \times 10^6$ PFU hMPV and further treated again with 50 µg of the previously mentioned corresponding antibodies. The neutralizing effect of TSLP and OX40L molecules in neutrophil recruitment in bronchoalveolar lavages (BALs) and replication in lungs were measured after 3 and 6 days post-infection. FIG. 6 A shows a significant reduction in neutrophil recruitment in BALs of hMPV-infected mice at day 3 post-infection as a result of using anti-TSLP or anti-OX40L monoclonal antibodies compared to those mice treated with control isotype. Furthermore, a significant reduction of hMPV N-gene transcript RNA levels in mice treated with anti-OX40L was observed on day 3 and 6 post-infection (FIGS. 6C and 6D). In addition, a significant reduction in viral load was observed on day 6 post-infection in mice treated with anti-TSLP.

Example 2

Assay of the Protective Effect of Treatment with Anti-Ly6G Neutralizing Antibodies after hMPV Infection This assay is directed to evaluate the protective effect of anti-Ly6G neutralizing monoclonal antibodies (1A8; Bio X Cell) present in neutrophils for reducing pulmonary inflammation and hMPV viral replication in WT mice and mice lacking TSLPR. Groups of WT and tslpr$^{-/-}$ BALB/c mice were treated with isotype control antibody (IgG2a) or anti-Ly6G antibody. As a result, a depletion of neutrophils in the blood, bronchioalveolar lavages (BALs) and lungs was observed for both WT and tslpr$^{-/-}$ BALB/c mice treated with anti-Ly6G, but not for those treated with control isotype (data not shown), indicating that neutrophil depletion functioned efficiently. These treated mice were intranasally inoculated either with mock or $1 \times 10^6$ PFU hMPV and 4 days post-infection, a portion of mouse lung tissue from each experimental group was fixed, prepared and stained with H&E. Cell infiltration in alveolar and peribronchial tissues were observed and evaluated for histopathologic score. Images obtained from each sample were double-blind evaluated for histopathology. In addition, the number of neutrophils in the walls and alveolar spaces (interstitial pneumonitis/alveolitis) and peribronchial areas (peribronchiolitis) was also counted in high power fields, in a total of 5 images per animal. Images of lung slices were obtained using an inverted microscope (CKX41, Olympus) and a Lumenerata Infinity 2 camera. A significant reduction in histopathological evaluation was observed in HMPV-infected WT mice treated with anti-Ly6G antibody compared to those treated with control isotype. In contrast, no difference was observed in hMPV-infected tslpr$^{-/-}$ mice between the two treated groups (FIG. 7A). This suggests that neutrophil depletion, by using anti-Ly6G neutralizing monoclonal antibody in WT mice, reduces inflammation and lung damage. In addition, the histopathological evaluation was similar to that observed with hMPV-infected tslpr$^{-/-}$ mice with or without neutrophil depletion. Furthermore, the number of neutrophils in both walls and alveolar spaces, and bronchioles was significantly lower in hMPV-infected WT and tslpr$^{-/-}$ mice treated with anti-Ly6G antibody compared to those treated with control isotype (FIGS. 7 B and C). These results suggest that the anti-Ly6G antibody is effective in decreasing inflammation and lung damage in hMPV-infected mice. In addition, the viral RNA was quantified in the lungs of each experimental group, i.e., hMPV-infected WT and tslpr$^{-/-}$ mice treated with anti-Ly6G antibody or with control isotype, by qRT-PCR using the specific primers for hMPV N-gene. Notably, we found a significant reduction of viral RNA copies in the lungs of hMPV-infected mice treated with anti-Ly6G antibody compared to those treated with isotype control, reaching similar levels to hMPV-infected tslpr$^{-/-}$ mice treated with control isotype (FIG. 7D). In addition, a viral load decrease was observed in hMPV-infected tslpr$^{-/-}$ mice treated with anti-Ly6G antibody compared to hMPV-infected WT mice treated with anti-Ly6G antibody (FIG. 7D). These results suggest that anti-Ly6G antibody significantly inhibits viral replication in the lungs of hMPV-infected mice and could have a synergistic effect with the lack of TSLPR.

The examples described in this Specification demonstrate the specificity and efficiency of these anti-TSLP, anti-OX40L and anti-CD177 monoclonal antibodies as treatment for ameliorating the symptoms and disease of individuals infected with human Metapneumovirus. The examples herein provided constitute a demonstration of some uses of the anti-TSLP, anti-TSLPR, anti-OX40L and anti-CD177 monoclonal antibodies, but, in no way, limit the scope of the present invention.

The invention claimed is:

1. Pharmaceutical composition for ameliorating the symptoms and disease of the respiratory infection caused by human Metapneumovirus (hMPV), comprising at least one agent that neutralizes the function of thymic stromal lymphopoietin (TSLP) and OX40L molecules, and a pharmaceutically acceptable excipient,
   wherein the agent that neutralizes the function of TSLP molecule is a monoclonal antibody comprising 3 heavy chain CDR sequences comprising SEQ ID NO: 1, SEQ ID NO: 2 and SEQ ID NO: 3, and 3 light chain CDR sequences comprising SEQ ID NO: 4, 5 and 6, or a monoclonal antibody having 3 heavy chain CDR sequences comprising SEQ ID NO: 7, SEQ ID NO: 8 and SEQ ID NO: 9, and 3 light chain CDR sequences comprising SEQ ID NO: 10, SEQ ID NO: 11 and SEQ ID NO: 12,
   wherein the agent that neutralizes the function of OX40L molecule is a monoclonal antibody having a light chain variable domain sequence comprising SEQ ID NO: 13 and a heavy chain variable domain sequence comprising SEQ ID NO: 14.

2. Pharmaceutical composition for ameliorating the symptoms and disease of the respiratory infection caused by human Metapneumovirus (hMPV), according to claim 1, wherein the agents neutralize the function of TSLP and OX40L molecule present in human neutrophils.

3. Method of therapeutic treatment for ameliorating the symptoms and disease of the respiratory infection caused by human Metapneumovirus (hMPV), comprising administering the agents that neutralize the function of TSLP and OX40L molecules, wherein the inhibitory agents are humanized monoclonal antibodies,     wherein the agent that neutralizes the function of TSLP molecule is a monoclonal antibody comprising 3 heavy chain CDR sequences comprising SEQ ID NO: 1, SEQ ID NO: 2 and SEQ ID NO: 3, and 3 light chain CDR sequences comprising SEQ ID NO: 4, 5 and 6, or a monoclonal antibody having 3 heavy chain CDR sequences comprising SEQ ID NO: 7, SEQ ID NO: 8 and SEQ ID NO: 9, and 3 light chain CDR sequences comprising SEQ ID NO: 10, SEQ ID NO: 11 and SEQ ID NO: 12, and     wherein the agent that neutralizes the function of OX40L molecule is a monoclonal antibody having a light chain variable domain sequence comprising SEQ ID NO: 13 and a heavy chain variable domain sequence comprising SEQ ID NO: 14.

4. Method of therapeutic treatment for ameliorating the symptoms and disease of the respiratory infection caused by human Metapneumovirus (hMPV) according to claim 3, wherein each one of the monoclonal antibodies, separately or together, simultaneously, are administered for treating patients infected with hMPV.

5. Method of therapeutic treatment for ameliorating the symptoms and disease of the respiratory infection caused by human Metapneumovirus (hMPV) according to claim 4, wherein the monoclonal antibodies are administered intranasally, orally, intravenously or intraperitoneally, so as to reduce the disease symptoms and not experience side effects from the treatment.

6. Method of therapeutic treatment for ameliorating the symptoms and disease of the respiratory infection caused by human Metapneumovirus (hMPV) according to claim 4, wherein the treatment reduces inflammation, damage and viral replication in the lungs.

* * * * *